US008183369B2

(12) United States Patent
Quigley et al.

(10) Patent No.: US 8,183,369 B2
(45) Date of Patent: May 22, 2012

(54) 4-[3-(4-CYCLOPROPA NECARBO NYL-PIPERAZINE-I-CARBONYL)-4-FLUORO-BENZYL]-2H-PHTHALAZ IN-1-ONE

(75) Inventors: Kathryn Anne Quigley, Macclesfield (GB); Ezra John Still, West Lafayette, IN (US); Leonard Jesse Chyall, West Lafayette, IN (US)

(73) Assignee: Kudos Pharmaceuticals Limited, London (GB)

( * ) Notice: Subject to any disclaimer, the term of this patent is extended or adjusted under 35 U.S.C. 154(b) by 0 days.

(21) Appl. No.: 12/738,181

(22) PCT Filed: Oct. 17, 2008

(86) PCT No.: PCT/GB2008/003510
§ 371 (c)(1),
(2), (4) Date: Jul. 15, 2010

(87) PCT Pub. No.: WO2009/050469
PCT Pub. Date: Apr. 23, 2009

(65) Prior Publication Data
US 2010/0286157 A1 Nov. 11, 2010

Related U.S. Application Data

(60) Provisional application No. 60/980,508, filed on Oct. 17, 2007.

(51) Int. Cl.
*A61K 31/501* (2006.01)
*C07D 403/08* (2006.01)
*A61P 35/04* (2006.01)

(52) U.S. Cl. ............... 544/238; 514/252.02; 514/248

(58) Field of Classification Search .................. None
See application file for complete search history.

(56) References Cited

U.S. PATENT DOCUMENTS

| | | |
|---|---|---|
| 3,813,384 A | 5/1974 | Vogelsang et al. |
| 4,665,181 A | 5/1987 | Thomas et al. |
| 4,841,047 A | 6/1989 | Engel et al. |
| 5,032,617 A | 7/1991 | Lee et al. |
| 5,041,653 A | 8/1991 | Lee et al. |
| 5,215,738 A | 6/1993 | Lee et al. |
| 5,556,856 A | 9/1996 | Engel et al. |
| 5,587,384 A | 12/1996 | Zhang et al. |
| 5,648,355 A | 7/1997 | Theoharides |
| 5,817,674 A | 10/1998 | Clemence et al. |
| 5,854,264 A | 12/1998 | Anthony et al. |
| 5,854,265 A | 12/1998 | Anthony |
| 5,859,035 A | 1/1999 | Anthony et al. |
| 5,872,136 A | 2/1999 | Anthony et al. |
| 5,874,444 A | 2/1999 | West |
| 5,874,452 A | 2/1999 | Anthony |
| 5,880,128 A | 3/1999 | Doll et al. |
| 5,880,140 A | 3/1999 | Anthony |
| 5,883,105 A | 3/1999 | Anthony |
| 5,886,178 A | 3/1999 | Allen et al. |
| 5,939,557 A | 8/1999 | Anthony et al. |
| 6,004,979 A | 12/1999 | Clemence et al. |
| 6,011,035 A | 1/2000 | Snutch et al. |
| 6,051,574 A | 4/2000 | Anthony |
| 6,060,038 A | 5/2000 | Burns et al. |
| 6,063,930 A | 5/2000 | Dinsmore et al. |
| 6,080,870 A | 6/2000 | Anthony et al. |
| 6,197,785 B1 | 3/2001 | Jackson et al. |
| 6,294,533 B1 | 9/2001 | Snutch et al. |
| 6,310,059 B1 | 10/2001 | Snutch |
| 6,340,684 B1 | 1/2002 | Napoletano et al. |
| 6,387,897 B1 | 5/2002 | Snutch |
| 6,426,415 B1 | 7/2002 | Jackson et al. |
| 6,465,467 B1 | 10/2002 | Nilsson et al. |
| 6,476,048 B1 | 11/2002 | Szabo et al. |
| 6,492,375 B2 | 12/2002 | Snutch |
| 6,498,160 B2 | 12/2002 | Napoletano et al. |
| 6,514,983 B1 | 2/2003 | Li |
| 6,514,984 B1 | 2/2003 | Watanabe |
| 6,552,016 B1 | 4/2003 | Baxter et al. |
| 6,617,322 B2 | 9/2003 | Snutch |
| 6,635,642 B1 | 10/2003 | Jackson et al. |
| 6,677,333 B1 | 1/2004 | Seko et al. |
| 6,891,041 B2 | 5/2005 | Petrov et al. |
| 6,943,168 B2 | 9/2005 | Snutch et al. |
| 6,949,554 B2 | 9/2005 | Snutch et al. |
| 6,951,862 B2 | 10/2005 | Snutch et al. |
| 6,953,857 B2 | 10/2005 | Will et al. |
| 7,064,128 B2 | 6/2006 | Snutch et al. |
| 7,067,665 B2 | 6/2006 | Nazare et al. |

(Continued)

FOREIGN PATENT DOCUMENTS

DE 2143745 3/1973

(Continued)

OTHER PUBLICATIONS

Norris, James F. in Experimental Organic Chemistry, 2nd Edition, McGraw-Hill Book Company, Inc. New York, 1924.*
United States Patent Office Action for U.S. Appl. No. 12/500,900 dated Sep. 14, 2011 (7 pages).
Affar, E. B. et al., "Immunodot blot method for the detection of poly(ADP-ribose) synthesized in vitro and in vivo," *Anal. Biochem* (1998) 259(2):280-283.
Al-Dabbagh and Smith, "Species differences in oxidative drug metabolism: some basic considerations." *Archives of toxicology*, Supplement. *Archiv fur Toxikologie*. Supplement, vol. 7, 219-231 (1984).

(Continued)

*Primary Examiner* — Brandon Fetterolf
*Assistant Examiner* — Dennis Heyer
(74) *Attorney, Agent, or Firm* — Michael Best & Friedrich LLP

(57) ABSTRACT

4-[3-(4-cyclopropanecarbonyl-piperazine-1-carbonyl)-4-fluoro-benzyl]-2H-phthalazin-1-one as crystalline Form L, methods of obtaining form L, pharmaceutical compositions comprising Form L and methods of using Form L and compositions comprising Form L.

8 Claims, 2 Drawing Sheets

U.S. PATENT DOCUMENTS

| | | | |
|---|---|---|---|
| 7,071,180 B2 | 7/2006 | Nilsson et al. |
| 7,151,102 B2 | 12/2006 | Martin et al. |
| 7,186,726 B2 | 3/2007 | Snutch et al. |
| 7,196,085 B2 | 3/2007 | Martin et al. |
| 7,407,957 B2 | 8/2008 | Javaid et al. |
| 7,449,464 B2 | 11/2008 | Martin et al. |
| 7,662,818 B2 | 2/2010 | Martin et al. |
| 7,692,006 B2 | 4/2010 | Menear et al. |
| 2001/0029258 A1 | 10/2001 | Snutch |
| 2003/0022819 A1 | 1/2003 | Ling et al. |
| 2003/0045530 A1 | 3/2003 | Snutch |
| 2003/0092694 A1 | 5/2003 | Nilsson et al. |
| 2003/0195192 A1 | 10/2003 | Haviv et al. |
| 2003/0195195 A1 | 10/2003 | Haviv et al. |
| 2004/0014744 A1 | 1/2004 | Haviv et al. |
| 2004/0023949 A1 | 2/2004 | Baxter et al. |
| 2004/0034035 A1 | 2/2004 | Snutch et al. |
| 2004/0044004 A1 | 3/2004 | Snutch et al. |
| 2004/0147529 A1 | 7/2004 | Snutch et al. |
| 2004/0192703 A1 | 9/2004 | Snutch et al. |
| 2004/0209872 A1 | 10/2004 | Snutch et al. |
| 2004/0242554 A1 | 12/2004 | Nilsson et al. |
| 2004/0259866 A1 | 12/2004 | Snutch et al. |
| 2004/0266784 A1 | 12/2004 | Snutch et al. |
| 2005/0020583 A1 | 1/2005 | Pulici |
| 2005/0054568 A1 | 3/2005 | Ling et al. |
| 2005/0080096 A1 | 4/2005 | Ishida et al. |
| 2005/0227919 A1 | 10/2005 | Ashworth et al. |
| 2005/0227999 A1 | 10/2005 | Pajouhesh et al. |
| 2005/0277629 A1 | 12/2005 | Lansbury et al. |
| 2006/0030557 A1 | 2/2006 | Haviv et al. |
| 2006/0084660 A1 | 4/2006 | Snutch et al. |
| 2006/0142293 A1 | 6/2006 | Martin et al. |
| 2006/0276391 A1 | 12/2006 | Auricchio et al. |
| 2007/0093489 A1 | 4/2007 | Javaid et al. |
| 2007/0185105 A1 | 8/2007 | Snutch et al. |
| 2008/0255128 A1 | 10/2008 | Javaid et al. |
| 2009/0270617 A1 | 10/2009 | Menear et al. |

FOREIGN PATENT DOCUMENTS

| | | |
|---|---|---|
| DE | 3813531 | 4/1988 |
| DE | 287 032 | 2/1991 |
| EP | 0030861 | 6/1981 |
| EP | 0269968 | 6/1988 |
| EP | 0355750 | 2/1990 |
| EP | 0389995 | 10/1990 |
| EP | 0502575 | 9/1992 |
| EP | 0590551 | 4/1994 |
| EP | 0634404 | 1/1995 |
| EP | 0699754 | 3/1996 |
| EP | 0705903 | 4/1996 |
| EP | 0792643 | 9/1997 |
| EP | 1477175 | 11/2004 |
| EP | 1760071 | 3/2007 |
| FR | 2262513 | 9/1975 |
| GB | 721286 | 1/1955 |
| GB | 2384776 | 3/2004 |
| IT | MI98A001671 | 4/1999 |
| JP | 54156526 | 12/1979 |
| JP | 58164577 | 9/1983 |
| JP | 62-252774 | 11/1987 |
| JP | 2005-154306 A * | 6/2005 |
| WO | WO 91/18591 | 12/1991 |
| WO | WO 93/14086 | 7/1993 |
| WO | WO 94/10151 | 5/1994 |
| WO | WO 95/24379 | 9/1995 |
| WO | WO 96/19225 | 6/1996 |
| WO | WO 96/31501 | 10/1996 |
| WO | WO 97/36587 | 10/1997 |
| WO | WO 97/38664 | 10/1997 |
| WO | WO 97/45412 | 12/1997 |
| WO | WO 98/43477 | 10/1998 |
| WO | WO 98/51308 | 11/1998 |
| WO | WO 99/08680 | 2/1999 |
| WO | WO 99/11624 | 3/1999 |
| WO | WO 99/11645 | 3/1999 |
| WO | WO 99/11649 | 3/1999 |
| WO | WO 99/44612 | 9/1999 |
| WO | WO 99/47494 | 9/1999 |
| WO | WO 00/05219 | 2/2000 |
| WO | WO 00/42040 | 7/2000 |
| WO | WO 00/44726 | 8/2000 |
| WO | WO 00/67734 | 11/2000 |
| WO | WO 01/10856 | 2/2001 |
| WO | WO 01/12199 | 2/2001 |
| WO | WO 01/16136 | 3/2001 |
| WO | WO 01/16137 | 3/2001 |
| WO | WO 01/21615 | 3/2001 |
| WO | WO 01/23390 | 4/2001 |
| WO | WO 01/57038 | 8/2001 |
| WO | WO 01/79184 | 10/2001 |
| WO | WO 01/85686 | 11/2001 |
| WO | WO 01/85687 | 11/2001 |
| WO | WO 01/87845 | 11/2001 |
| WO | WO 01/90077 | 11/2001 |
| WO | WO 02/36576 | 5/2002 |
| WO | WO 03/070726 | 5/2002 |
| WO | WO 02/44157 | 6/2002 |
| WO | WO 02/068407 | 9/2002 |
| WO | WO 02/090334 | 11/2002 |
| WO | WO 02/094790 | 11/2002 |
| WO | WO 03/007959 | 1/2003 |
| WO | WO 03/051879 | 6/2003 |
| WO | WO 03/055865 | 7/2003 |
| WO | WO 03/057145 | 7/2003 |
| WO | WO 03/063874 | 8/2003 |
| WO | WO 03/070707 | 8/2003 |
| WO | WO 03/080581 | 10/2003 |
| WO | WO 03/093261 | 11/2003 |
| WO | WO 2004/080976 * | 9/2004 |
| WO | WO 2005/053662 | 6/2005 |
| WO | WO 2006/097176 | 9/2006 |
| WO | WO 2008/083027 | 7/2008 |

OTHER PUBLICATIONS

Ame, J.-C. et al., "PARP-2, a novel mammalian DNA damage-dependent poly(ADP-ribose) polymerase," *J. Biol. Chem.* (1999) 274(25):17860-17868.

Ame, J.-C. et al., "The PARP superfamily," BioEssays (2004) 26:882-893.

Angell, S.M. et al., "Consistent gene silencing in transgenic plants expressing a replicating potato virus X RNA," *EMBO J.* (1997) 16(12):3675-3684.

Arnaudeau, C. et al., "DNA double-strand breaks associated with replication forks are predominantly repaired by homologous recombination involving an exchange mechanism in mammalian cells," *J. Mol. Biol* (2001) 307:1235-1245.

Banasik, M. et al., "Specific Inhibitors of Poly (ADP-Ribose) Synthetase and Mono (ADP-Ribosyl) transferse", *J. Biol. Chem.*, 1992, vol. 267, 1569-1575.

Banasik, M. et al., "Inhibitors and activators of ADP-ribosylation reactions," *Mol. Cell Biochem.* (1994) 138:185-197.

Banker, G.S. et al., Modern Pharmaceutics, Third Edition, Marcel Dekker, Inc., New York, (1996) p. 596.

Ben-Hur, E. et al , "Inhibitors of poly (ADP-ribose) synthesis enhance radiation response by differentially affecting repair of potentially lethal versus sublethal damage," Br. J. Cancer (1984) 49(VI):39-42.

Berge et al., 1977, "Pharmaceutically Acceptable Salts," *J. Pharm. Sci.*, vol. 66, 1-19. Protective Groups in Organic Synthesis (T. Green and P. Wuts, Wiley, 1991).

Berger, N. A. et al., "Poly (ADP-ribose) in cellular response to DNA damage", *Radiation Research*, 1985, vol. 101, 4-14.

Bhattacharyya, A. et al., "The breast cancer susceptibility gene BRCA1 is required for subnuclear assembly of Rad51 and survival following treatment with the DNA cross-linking agent cisplatin," *J. Biol. Chem.* (2000) 275(31: 23899-23903.

Bloch, W. et al., "Poly-adenosine diphosphate-ribose polymerase inhibition for myocardial protection: pathophysiologic and physiologic considerations," J. Thoracic Card. Surg. (2004) 128(2):323-324.

Bold, G. et al., "New anilinophthalazines as potent and orally well absorbed inhibitors of the VEGF receptor tyrosine kinases useful as antagonists of tumor-driven angiogenesis," J. Med. Chem. (2000) 43:3200 (Abstract).

Bold, G. et al., "New anilinophthalazines as potent and orally well absorbed inhibitors of the FEBF receptor tyrosine kinases useful as antagonists of tumour-driven angiogenesis", *J. Med. Chem.*, 2000, vol. 43, No. 12, 2310-2323.

Bowman et al., "Differential effects of the poly (ADP-ribose) polymerase (PARP) inhibitor NU 1025 on topoisomerase I and II inhibitor cytotoxicity in L1210 cells in vitro," *British Journal of Cancer*, vol. 84(1), 106-112 (2001).

Braga, D. et al., "Making crystals from crystals: a green route to crystal engineering and polymorphism," Chem. Commun. (2005) 3635-3645.

Brummelkamp, T. R. et al., "A system for stable expression of short interfering RNAs in mammalian cells," *Science* (2002) 296:550-553.

Burzio, L. et al., "Poly (adenosine diphosphoribose) synthase activity of isolated nuclei of normal and leukemic leukocytes (38930)", *Proc. Soc. Exp. Bio. Med.*, 1975, vol. 149, 933-938.

Calabrese, C.R. et al., "Identification of potent nontoxic poly(ADP-ribose) polymerase-1 inhibitors: chemopotentiation and pharmacological studies," Clin. Can. Res. (2003) 9:2711-2718.

Caldecott, K.W., "DNA single-strand break repair and spinocerebellar ataxia," Cell (2003) 112:7-10.

Cantoni, O. et al., "Hydrogen peroxide insult in cultured mammalian cells: relationships between DNA single-strand breakage, poly (ADP-ribose) metabolism and cell killing", *Biochim. Biophys. Acta*, 1989, vol. 1014, 1-7.

Catteau, A. et al., "Methylation of the BRCA1 promoter region in sporadic breast and ovarian cancer: correlation with disease characteristics," *Oncogene* (1999) 18:1957-1965.

Chalmers, A.J. , "Poly(ADP-ribose) polymerase-1 and ionizing radiation: sensor, signaller and therapeutic target," Clin. Onc. (2004) 16:29-39.

Chappuis, P. O. et al., "Risk Assessment and Genetic Testing," *Cancer Treat. Res.*, 2002, vol. 107, 29-59.

Chiarugi, A., "Poly(ADP-ribose) polymerase: killer or conspirator? The 'suicide hypothesis' revisted," Trends in Pharm. Sci. (2002) 23(3):122-129.

Cockcroft, X-L. et al., "Phthalazinones 2: optimisation and synthesis of novel potent inhibitors of poly(ADP-ribose)polymerase," Biorg. Med. Chem. Lett. (2006) 16:1040-1044.

Cosi, C. et al., "Poly (ADP-ribose) polymerase: early involvement in glutamate-induced neurotoxicity in cultured cerebellar granule cells", *J.Neurosci. Res.*, 1994, vol. 39, 38-46.

Cosi, C., "New inhibitors of poly(ADP-ribose) polymerase and their potential therapeutic targets," Expert Opin. Ther. Patents (2002) 12(7): 1047-1071.

Couzin, J., "The twists and turns in BRCA's path," Science (2003) 302:591-592.

Crooke, S.T., "Therapeutic applications of oligonucleotides," *Ann. Rev. Pharmacol. Toxicol.* (1992) 32:329-376.

Cuzzocrea, S., "Shock, inflammation and PARP," Pharmacological Res. (2005) 52:72-82.

D'Adda Di Fagagna, F. et al., "Functions of poly(ADP-ribose) polymerase in controlling telomere length and chromosomal stability", *Nature Gen.*, 1999, vol. 23, No. 1, 76-80.

D'Amours, D. et al., "Poly(ADP-ribosyl)ation reactions in the regulation of nuclear functions", *Biochem. J.*, 1999, vol. 342, 249-268.

D'Amours, D. et al., "The MRE11 complex: at the crossroads of DNA repair and checkpoint signalling," Mol. Cell Biol. (2002) 3:317-327.

D'Andrea, A. D. et al., "The fanconi anaemia/BRCA pathway," *Nat. Rev. Cancer* (2003) 3:23-34.

Dantzer, F. et al., "Base excision repair is implied in mammalian cells lacking poly(ADP-ribose) polymerase-1," *Biochemistry* (2000) 39:7559-7569.

Dantzer, F. et al., "Involvement of poly(ADP-ribose) polymerase in base excision repair," Biochimie (1999) 81:69-75.

Davies, A. A. et al., "Role of BRCA2 in control of the RAD51 recombination and DNA repair protein," *Mol. Cell* (2001) 7:273-282.

Dillon, K. J. et al., "A flashplate assay for the identification of PARP-1 inhibitors," *J. Biomolecular Screening* (2003) 8(3):347-352.

Durkacz, B. W. et al., "(ADP-ribose)$_n$ participates in DNA excision repair", *Nature*, 1980, vol. 283, No. 7, 593-596.

Dusemund, "Isochino [3,2-a]phthalazin-5,8-dione", Arch. Pharm., (Weinhein) 1982, pp. 925-930. (English Abstract).

Dusemund, J., "Einfache synthese von isochino[2,3-c][2,3]benzoxazepinon und -[2,3]benzodiazepinonen sowie ihrer vorstufen," Arch. Pharm. (1988) 321:41-44.

Egawa, C. et al., "Decreased expression of BRCA2 mRNA predicts favorable response to docetaxel in breast cancer," Int. J. Cancer (2001) 95:255-259.

Egawa, C. et al., "Quantitative analysis of estrogen receptor-60 and -β messenger RNA expression in normal and malignant thyroid tissues by real-time polymerase chain reaction," Oncology (2001) 61:293-298.

Ehrlich, H.A. et al., "Recent advances in the polymerase chain reaction," *Science* (1991) 252:1643-1650.

Elbashir, S. M. et al., "Duplexes of 21-nucleotide RNAs mediate RNA interference in cultured mammalian cells," *Nature* (2001) 411:494-498.

El-Tamaty et al., Synthesis and biological activity of some 4-benzyl-1(2H)-phthalazinone derivatives, *Indian J. Chemistry*, v. 35B, 1067-1072 (1996).

El-Tamaty, E-S.H. et al., "Synthesis and biological activity of some 4-benzyl-1(2H)-phthalazinone derivatives," Chem. Abs. (1996) 125:23, 125:300924j.

Esteller, M. et al., "Promoter hypermethylation and BRCA1 inactivation in sporadic breast and ovarian tumors," *J. Natl. Cancer Inst.* (2000) 92(7):564-569.

Ferraris, D. et al., "Design and synthesis of poly ADP-ribose polymerase-1 inhibitors. 2. Biological evaluation of Aza-5[H]-phenanthridin-6-ones as potent, aqueous-soluble compounds for the treatment of ischemic injuries," J. Med. Chem. (2003) 46:3138-3151.

Fire, A. et al., "Potent and specific genetic interference by double-stranded RNA in *Caenorhabditis elegans*," *Nature* (1998) 391:806-811.

Foray, N. et al., "A subset of ATM- and ATR-dependent phosphorylation events requires the BRCA1 protein," *Embo J.* (2003) 22(11):2860-2871.

Fujisawa Pharmaceutical Co., "Preaparation of 2-carboxyalkyl-4-aralkylphthalazine derivatives as aldose reductase inhibitors and a process for preparing them," Chemical Abstracts 109:6531.

Fuska, J. et al., "New Cytotoxic and antitumor agents," *Chemical Abstracts*, 104:102050 (1985).

Gaken. J. A. et al., "Efficient retroviral infection of mammalian cells is blocked by inhibition of poly(ADP-ribose) polymerase activity", *J. Virology*, 1996, vol. 70, No. 6, 3992-4000.

Gale, P.A. et al., "Calixpyrroles II," Coordination Chem. Rev. (2001) 222:57-102.

Gavezzotti, A., "Are crystal structures predictable?" Acc. Chem. Res. (1994) 27:309-314.

Greene, T.W. et al., Protective Groups in Organic Synthesis, Chapters 2 and 7, John Wiley & Sons Inc. (1999) p. 17-23 and 494-503.

Griffin, C.S. et al., "Mammalian recombination-repair genes XRCC2 and XRCC3 promote correct chromosome segregation," Nature Cell Biol. (2000) 2:757-761.

Griffin et al., "The role of inhibitors of poly (ADP-ribose) polymerase as resistance-modifying agents in cancer therapy," *Biochim* vol. 77, 408-422 (1995).

Grube, K. et al., "Direct stimulation of poly(ADP ribose) polymerase in permeabilized cells by double-stranded DNA oligomers," Anal Biochem. (1991) 193:236-239.

Haber, J. E., "DNA recombination: the replication connection," *Trends Biochem. Sci.* (1999) 24:271-275.

Hall, I.H. et al., "Cytotoxicity of imides-N-alkyl semicarbazones, thiosemicarbazones, acetylhydrazones and related derivatives," *Anti-Cancer Drugs* (and abstract 122:204573), V.6, 147-153 (1995).

Halldorsson, H. et al., "Poly(ADP-ribose) polymerase activity in nucleotide permeable cells," FEBS Lett. (1978) 85(2):349-352.

*Hawley's Condensed Chemical Dictionary*, 13$^{th}$ ed., Van Nostrand Reinhold eds. 716 and 825 (1997).

Herceg, Z. et al., "Functions of poly(ADP-ribose) polymerase (PARP) in DNA repair, genomic intergirty and cell death," Mut. Res. (2001) 477:97-110.

Hirai, K. et al., "Aberration of poly(adenosine diphosphate-ribose) metabolism in human colon adenomatous polyps and cancers", Cancer Res., 1983, vol. 43, 3441-3446.

Hiramoto, T. et al., "Mutations of a novel human RAD54 homologue, RAD54B, in primary cancer," Oncogene (1999) 18:3422-3426.

Hoeijmakers, J. H.J., "Genome maintenance mechanisms for preventing cancer," Nature (2001) 411:366-374.

Hughes-Davies, L. et al., "EMSY links the BRCA2 pathway to sporadic breast and ovarian cancer," Cell (2003) 115:523-535.

Iino, M. et al., "Rational design and evaluation of new lead compound structures for selective .beta.ARK1 inhibitors," J. Med. Chem. (2002) 45(11):2150-2159.

Islam, A.M. et al., "Thioarylidenephthalides and related compounds: Part II. Reactions with amino compounds," Chemical Abstracts (1977) 87:67943.

Islam, A.M. et al., "4, 5, 6, 7-Tetraiodo-3-benzalphthalides and related compounds," (1981) Chemical Abstracts 95:187182.

Islam, A.M. et al., "Action of phosphorus pentasulfide on the products of interaction of p-sulfamoylphenylacetic acids with phthalic anhydride," (1981) Chemical Abstracts 95:62106.

Jackson, S.P., "Sensing and repairing DNA double-strand breaks," Carcinogenesis (2002) 23(5):687-696.

Janatova, M. et al., "Detection of the most frequent mutations in BRCA1 gene on polyacrylamide gels containing spreadex polymer NAB," Neoplasma (2003) 50(4):246-250.

Jancarkova, N., "Detection and incidence of mutations of BRCA1 gene in patients with cancer of the breast and ovary," Ceska Gynekol. (2003) 68(1):11-16.

Jantzen and Robinson, "B. Prodrugs," taken from Modern Pharmaceutics, Third Edition, Banker and Rhodes, editors (1996) p. 596.

Jasin, M., "Homologous repair of DNA damage and tumorigenesis: the BRCA connection," Oncogene (2002) 21(58):8981-8993.

Jijon, H.B. et al., "Inhibition of poly(ADP-ribose) polymerase attenuates inflammation in a model of chronic colitis," Am. J. Physiol. Gastrointest. Liver Physiol. (2000) 279:G641-G651.

Johnson, R.D. et al., "Mammalian XRCC2 promotes the repair of DNA double-strand breaks by homologous recombination," Nature (1999) 401:397-399.

Kanaar, R. et al., "Molecular mechanisms of DNA double-strand break repair," Trends Cell Biol. (1998) 8:483-489.

Kashani-Sabet, M. et al., "Application of ribozymes to cancer gene therapy," Cancer Gene Therapy (1995) 2(3):213-223.

Kawamura, I. et al., "Ponalrestat, an aldose reductase inhibitor," Chemical Abstract 132:273943.

Kerr, P. et al., "New complexities for BRCA1 and BRCA2," Curr. Biol. (2001) 11:R668-676.

Kerrigan, F. et al. "Imide-substituted 4-benzyl-2H-phthalazin-l-ones: potent inhibitors of poly(ADP-ribose) polymerase-1 (PARP-1)," Poster at 12th SCI-RSC Medicinal Chemistry Symposium, Cambridge, 7-10 (2003).

Khanna, K. K. et al., "DNA double-strand breaks: signaling, repair and the cancer connection," Nat. Genet. (2001) 27(3):247-254.

Kraakman-Van Der Zwet, M. et al., "Brca2 (XRCC11) deficiency results in radioresistant DNA synthesis and a higher frequency of spontaneous deletions," Mol. Cell Biol. (2002) 22(2):669-679.

Kuperstein, G. et al., "A rapid fluorescent multiplexed-PCR analysis (FMPA) for founder mutations in the BRCA1 and BRCA2 genes," Clin. Genet. (2000) 57:213-220.

Kupper, J-H. et al., "Trans-dominant inhibition of poly(ADP-ribosyl)ation potentiates carcinogen-induced gene amplification in SV40-transformed Chinese hamster cells," Cancer Res. (1996) 56:2715-2717.

Lakhani, S. R. et al., "The pathology of familial breast cancer: predictive value of immunohistochemical markers estrogen receptor, progesterone receptor, HER-2, and p53 in patients with mutations in BRCA1 and BRCA2," J. Clin. Oncol. (2002) 20(9):2310-2318.

Le Rhun, Y. et al., "Cellular responses to DNA damage in the absence of poly(ADP-ribose)polymerase", Biochem. Biophys. Res. Commun., 1998, vol. 245, 1-10.

Lemay, M. et al., "Detection of DNA damage and identification of UV-induced photoproducts using the cometassay kit," Biotechniques (1999) 27:846-851.

Liaudet, L. et al., "Protection against hemorrhagic shock in mice genetically deficient in poly(ADP-ribose)polymerase", Proc. Natl. Acad. Sci. U.S.A., 2000, vol. 97, No. 3, 10203-10208.

Lindahl, T. et al, "Quality control by DNA repair," Science (1999) 286:1897-1905.

Lindahl, T. et al, "Post-translational modification of poly(ADP-ribose) polymerase induced by DNA strand breaks," TIBS (1995) 20:405-411.

Loh, V.M. et al., "Phthalazinones. Part 1: The design and synthesis of a novel series of potent inhibitors of poly(ADP-ribose)polymerase," Bioorg. Med. Chem. Lett. (2005) 15:2235-2238.

Lundin, C. et al., "Different roles for nonhomologous end joining and homologous recombination following replication arrest in mammalian cells," Mol. Cell. Biol. (2002) 22(16):5869-5878.

Lundin, C. et al., "RAD51 is involved in repair of damage associated with DNA replication in mammalian cells," J. Mol. Biol. (2003) 328:521-535.

Magnusson, J. et al , "Inhibitor of poly(ADP-ribose)transferase potentiates the recombinogenic but not the mutagenic action of alkylating agents in somatic cells in vivo in drosophila melanogaster," Mutagenesis (1990) 5(5):511-514.

Martin, N. et al., "Phthalazinone derivatives as potent PARP-1 inhibitors", 13th Intl. Symposium on ADP-ribosylation, 2001, Abstract 107.

Martin, N. et al., "DNA repair inhibition and cancer therapy," J. Photochem. and PhotoBiol. B: Biology (2001) 63:162-170.

Matsuda, M. et al., "Mutations in the RAD54 recombination gene in primary cancers," Oncogene(1999) 18:3427-3430.

McMahon, G., "VEGF receptor signaling in tumor angiogenesis," The Oncologist (2000) 5(suppl 1):3-10.

McNealy, T. et al., "Intrinsic presence of poly (ADP-ribose) is significantly increased in malignant prostate compared to benign prostate cell lines," Anticancer Res. (2003) 23:1473-1478.

Menear, K.A. et al., "4-[3-(4-cyclopropanecarbonylpiperazine-l-carbonyl)-4-fluorobenzyl]-2H-phthalazin-1-one: a novel bioavailable inhibitor of poly(ADP-ribose) polymerase-1,"J. Med. Chem. (Published on Web (Sep. 19, 2008) A-K.

Menissier De Murcia, J. et al., "Requirement of poly(ADP-ribose)polymerase in recovery from DNA damage in mice and cells", Proc. Natl. Acad. Sci. U.S.A., 1997, vol. 94, 7303-7307.

Menissier De Murcia, J. et al., "Functional interaction between PARP-1 and PARP-2 in chromosome stability and embryonic development in mouse," EMBO J. (2003) 22(9):2255-2263.

Mercola, D. et al., "Antisense approaches to cancer gene therapy," Cancer Gene Therapy (1995) 2(1):47-59.

Miller, B.A. , "Inhibition of TRPM2 function by PARP inhibitors protects cells from oxidative stress-induced death," Br. J. Pharmacology (2004) 143:515-516.

Miwa, M. et al., "Cell density-dependent increase in chromatin-associated ADP-ribosyltransferase activity in simian virus 40-transformed cells", Arch. Biochem. Biophys., 1977, vol. 181, 313-321.

Morrison, C. et al., "Genetic interaction between PARP and DNA-PK in V(D)J recombination and tumorigenesis," Nature Genetics (1997) 17:479-482.

Moynahan, M. E. et al., "Brca 1 controls homology-directed DNA repair," Mol. Cell (1999) 4:511-518.

Moynahan, M. E. et al., "BRCA2 is required for homology-directed repair or chromosomal breaks," Mol. Cell (2001) 7:263-272.

Mullis, K. et al., "Specific enzymatic amplification of DNA in vitro: the polymerase chain reaction," Cold Spring Harbor Symp. Quant. Biol. (1987) 51:263-273.

Nakamura, J. et al., "Quantitation of intracellular NAD(P)H can monitor an imbalance of DNA single strand break repair in base excision repair deficient cells in real time," Nuc. Acids Res. (2003) 31(17):e104 1-7.

Nathanson, K. L. et al., "Breast cancer genetics: what we know and what we need," Nat. Med. (2001) 7(5):552-556.

Neuhausen, S. L. et al., "Mutation testing of early-onset breast cancer genes BRCA1 and BRCA2," Genet. Test (1997) 1(2):75-83.

Noel, G. et al., "Poly(ADP-ribse) polymerase (PARP-1) is not involved in DNA double-strand break recovery," BMC Cell Biol. (2003) 4:7-17.

Pacher et al., "The Role of Poly(ADP-Ribose) Polymerase Activation in the Development of Myocardial and Endothelial Dysfunction in Diabetes," *Diabetes*, 51:514-521 (2002).

Perkins, E. et al., "Novel inhibitors of poly(ADP-ribose)polymerase/PARP1 and PARP2 identified using a cell-based screen in yeast", *Cancer Res.*, vol. 61, 4175-4183 (2001).

Pierce, A.J. et al., "XRCC3 promotes homology-directed repair of DNA damage in mammalian cells," Genes & Dev. (1999) 13:2633-2638.

Pinedo et al., "Translation research . . . " The Oncologist (2000) 5(suppl 1):1-2.

Radice, P. J., "Mutations of BRCA genes in hereditary breast and ovarian cancer," *Exp. Clin. Cancer Res.* (2002) 21(3 Suppl.):9-12.

Rattan, S. I. et al., "Kinetin delays the onset of ageing characteristics in human fibroblasts", *Biochem. Biophys. Res. Commun.*, 1994, vol. 201, No. 2, 665-672.

Said, S. I. et al., "Excitotoxicity in the lung: N-methy-D-aspartate-induced, nitric oxide-dependent, pulmonary edema is attenuated by vasoactive intestinal peptide and by inhibitors of poly(ADP-ribose)polymerase", *Proc. Natl. Acad. Sci. U.S.A.*, 1996, vol. 93, 4688-4692.

Samper, E. et al., "Normal telomere length and chromosomal end capping in poly(ADP-ribose) polymerase-deficient mice and primary cells despite increased chromosomal instability," J. Cell Biol. (2001) 154(1):49-60.

Satoh, M.S. et al., "Role of poly(ADP-ribose) formation in DNA repair," Nature (1992) 356:356-358.

Schlicker, A. et al., "4-Amino-1,8-napthalimide: a novel inhibitor of poly(ADP-ribose)polymerase and radiation sensitizer", *Int. J. Radiat. Bio.*, 1999, vol. 75, No. 1, 91-100.

Schreiber, V. et al., "A dominant-negative mutant of human poly(ADP-ribose) polymerase affects cell recovery, apoptosis, and sister chromatid exchange following DNA damage," Proc. Natl. Acad. Sci. USA (1995) 92:4753-4757.

Schreiber, V. et al., "Poly(ADP-ribose) polymerase-2 (PARP-2) is required for efficient base excision DNA repair in association with PARP-1 and XRCC1," J. Biol. Chem. (2002) 277(25):23028-23036.

Schultz, N. et al., "Poly(ADP-ribose) polymerase (PARP-1) has a controlling role in homologous recombination," *Nucleic Acids Res.* (2003) 31:4959-4964.

Semionov, A. et al., "Inhibition of poly(ADP-ribose)polymerase stimulates extrachromosomal homologous recombination in mouse Ltk-fibroblasts," Nuc. Acids Res. (1999) 27(22):4526-4531.

Shah, G.M. et al., "Complete inhibition of poly(ADP-ribose) polymerase activity prevents the recovery of C3H10T1/2 cells from oxidative stress," Biochimica et Biophysica Acta (1996) 1312:1-7.

Shall, S. et al., "Poly(ADP-ribose) polymerase-1: what have we learned from the deficient mouse model?" *Mutat. Res.* (2000) 460:1-15.

Shimizu, T. et al., "Inhibitory effects of azelastine and tranilast on leukotriene $B_4$ and leukotriene $C_4$ generation by rat colonic mucosa", *Prostaglandins Leukotrienes and Essential Fatty Acids*, 1995, vol. 53, 355-358.

Silverman, R.B., *The Organic Chemistry of Drug Design and Drug Action*, 352-400 (1992) Academic Press, Inc.

Simbulan-Rosenthal, C.M. et al., "Chromosomal aberrations in PARP-/-mice: genome stabilization in immortalized cells by reintroduction of poly(ADP-ribose) polymerase cDNA," Proc. Natl. Acad. Sci. USA (1999) 96(23):13191-13196.

Skehan, P. et al., "New colorimetric cytotoxicity assay for anticancer-drug screening", *J. Natl. Cancer Inst.*, 1990, vol. 82, No. 13, 1107-1112.

Southan, G.J. and Szabo, C., "Poly (ADP-ribose) polymerase inhibitors," *Current Medicinal Chemistry*, 10:4, 321-340 (2003).

Spears, L.G. Jr. et al., "Anionic phosphorous as a nucleophile. An anion chain arbuzov mechanism," J. Org. Chem. (1987) 52:61-64.

Suto, M.J. et al., "Dihydroisoquinolinones: the design and synthesis of a new series of potent inhibitors of poly(ADP-ribose) polymerase," *Anticancer Drug Des.* (1991) 7:107-117.

Szabo, C. et al., "Endothelial dysfunction in a rat model of endotoxic shock", *J. Clin. Invest.*, 1997, vol. 100, 723-25.

Szabo, "PARP as a Therapeutic Target," Zhang, Ed. CRC Press (2002) 169-204.

Szabo, G. et al., "Poly-ADP-ribose polymerase inhibition protects against myocardial and endothelial reperfusion injury after hypothermic cardiac arrest," J. Thoracic Cardiovas. Surg. (2003) 126(3):651-658.

Taniguchi, T. et al., "Disruption of the Fanconi anemia-BRCA pathway in cisplatin-sensitive ovarian tumors," *Nat. Med.* (2003) 9(5):568-574.

Tarsounas, M. et al., "BRCA2-dependent and independent formation of RAD51 nuclear foci," *Oncogene* (2003) 22: 1115-1123.

Tasatargil, A. et al., "Poly(ADP-ribose) polymerase inhibition prevents homocysteine-induced endothelial dysfunction in the isolated rat aorta," Pharmacology (2004) 72:99-105.

Tebbs, R.S. et al., "Correction of chromosomal instability and sensitivity to diverse mutagens by a cloned cDNA of the XRCC3 DNA repair gene," Proc. Natl. Acad. Sci. USA (1995) 92:6354-6358.

Tentori, L. et al., "Potential clinical applications of poly(ADP-ribose) polymerase (PARP) inhibitors," Pharm. Res. (2002) 45(2):73-85.

Thompson, L. H. et al., "Recombinational DNA repair and human disease," *Mutat. Res.* (2002) 509:49-78.

Tracey, W. et al., "Aldose reductase inhibition alone or combined with an adenosine A3 agonist reduces ischemic myocardial injury," *Chemical Abstract* (2000) 134:65983.

Tutt, A. et al., "The relationship between the roles of BRCA genes in DNA repair and cancer predisposition," Trends Mol. Med. (2002) 8(12):571-576.

Tutt, A. et al., "Mutation in Brca2 stimulates error-prone homology-directed repair of DNA double-strand breaks occurring between repeated sequences," EMBO J. (2001) 20(17):4704-4716.

Tutt, A N.J. et al., "Disruption of Brca2 increases the spontaneous mutation rate in vivo: synergism with ionizing radiation," Embo Reports (2002) 3(3):255-260.

Uhlmann, E. et al., Antisense oligonucleotides: a new therapeutic principle, *Chem. Rev.* (1990) 90(4):543-584.

Van Gent, D.C. et al., "Chromosomal stability and the DNA double-stranded break connection," Nature Reviews (2001) 2:196-206.

Venkitaraman, A. R., "Cancer susceptibility and the functions of BRCA1 and BRCA2," *Cell* (2002) 108:171-182.

Vippagunta, S.R. et al., "Crystalline solids," Adv. Drug Delivery Reviews (2001) 48:3-26.

Virag and Szabo, "The Therapeutic Potential of Poly(ADP-Ribose) Polymerase Inhibitors," *Pharmacological Reviews*, vol. 54(3), (2002) 375-429.

Voinnet, O. et al. "Systemic signalling in gene silencing," *Nature* (1997) 389:553.

Waldman, A.S. et al., "Stimulation of intrachromosomal homologous recombination in mammalian cells by an inhibitor of poly(ADP-ribosylation)," Nuc. Acids Res. (1991) 19(21):5943-5947.

Wang, Z.-Q. et al., "Mice lacking ADPRT and poly(ADP-ribosyl)ation develop normally but are susceptible to skin disease", *Genes Dev.*, 1995, vol. 9, 509-520.

Wang, Z.-Q. et al., "PARP is important for genomic stability but dispensable in apoptosis," *Genes Dev.* (1997) 11:2347-2358.

West, A.R. "Solid State Chemistry and its Applications" Wiley, New York, 358 and 365 (1988).

Wolff, M.E., Burger's Medicinal Chemistry and Drug Discovery, Fifth Edition, vol. 1: Principles and Practice, John Wiley & Sons, Inc., New York (1995) 975-977.

Wood, R.D. et al., "Human DNA repair genes," *Science* (2001) 291:1284-1289.

Yamaguchi, M. et al., "Novel antiasthmatic agents with dual activities of thromboxane $A_2$ synthetase inhibition and bronchodilation. 1. 2-[2-(1-Imidazolyl)alkyl]-1(2*H*)-phthalazinones", *J. Med. Chem.*, 1993, vol. 36, No. 25, 4052-4060.

Yamaguchi, M. et al., "Novel antiasthmatic agents with dual activities of thromboxane $A_2$ synthetase inhibition and bronchodilation. 2. 4-(3-Pyridyl)-1(2*H*)-phthalazinones", *J. Med. Chem.*, 1993, vol. 36, No. 25, 4061-4068.

Zamore, P. D., "RNAi: double-stranded RNA directs the ATP-dependent cleavage of mRNA at 21 to 23 nucleotide intervals," *Cell* (2000) 101:25-33.

Zamore, P. D., "RNA interference: listening to the sound of silence," *Nature Structural Biology* (2001) 8(9):746-750.

Zhang, J. et al., "Neuroprotective effects of poly(ADP-ribose) polymerase inhibition on focal cerebral ischemia," Portland Press Proc. (1998) 15:125.

Zhang, W. et al., "Fluorous 2,4-dichloro-1,3,5-triazine (F-DCT) as amide coupling agent," QSAR Comb Sci. (2006) 25(8-9):724-727.

Zhong, Q. et al., "Association of BRCA1 with the hRad50-hMre11-p95 complex and the DNA damage response" Science (1999) 285:747-750.

Zingarelli, B. et al., "Activator protein-1 signalling pathway and apoptosis are modulated by poly(ADP-ribose) polymerase-1 in experimental colitis," Immunology (2004) 113:509-517.

United States Office Action for U.S. Appl. No. 10/021,506 dated Nov. 26, 2003 (5 pages).

United States Office Action for U.S. Appl. No. 10/021,506 dated Sep. 7, 2004 (7 pages).

United States Office Action for U.S. Appl. No. 10/021,506 dated Jun. 15, 2005 (5 pages).

United States Office Action for U.S. Appl. No. 10/021,506 dated Nov. 21, 2005 (8 pages).

United States Office Action for U.S. Appl. No. 11/352,178 dated Nov. 7, 2008 (11 pages).

United States Office Action for U.S. Appl. No. 11/352,178 dated Jun. 17, 2009 (9 pages).

United States Office Action for U.S. Appl. No. 10/426,147 dated Oct. 28, 2004 (32 pages).

United States Office Action for U.S. Appl. No. 10/426,147 dated Aug. 9, 2005 (16 pages).

United States Office Action for U.S. Appl. No. 10/426,147 dated Apr. 25, 2006 (14 pages).

United States Office Action for U.S. Appl. No. 11/873,671 dated Sep. 3, 2008 (35 pages).

United States Office Action for U.S. Appl. No. 11/873,671 dated Mar. 6, 2009 (12 pages).

United States Office Action for U.S. Appl. No. 12/143,208 dated May 8, 2009 (17 pages).

United States Office Action for U.S. Appl. No. 10/876,080 dated Jun. 23, 2005 (4 pages).

United States Office Action for U.S. Appl. No. 10/876,080 dated Jul. 12, 2006 (5 pages).

United States Office Action for U.S. Appl. No. 10/876,080 dated Jan. 5, 2007 (5 pages).

United States Office Action for U.S. Appl. No. 10/876,080 dated Oct. 4, 2007 (6 pages).

United States Office Action for U.S. Appl. No. 11/318,155 dated Jul. 11, 2008 (10 pages).

United States Office Action for U.S. Appl. No. 11/318,155 dated Jan. 26, 2009 (9 pages).

United States Patent Office Action for U.S. Appl. No. 12/500,900 dated Feb. 15, 2012 (6 pages).

US 6,759,401, 07/2004, Nilsson et al. (withdrawn)

* cited by examiner

4-[3-(4-CYCLOPROPANECARBONYL-PIPERAZINE-I-CARBONYL)-4-FLUORO-BENZYL]-2H-PHTHALAZIN-1-ONE

CROSS-REFERENCE TO RELATED APPLICATIONS

This patent application is a national stage filing under 35 U.S.C. 371 of International Application No. PCT/GB2008/003510, filed on Oct. 17, 2008, which claims priority benefits to U.S. Provisional Application No. 60/980,508, filed on Oct. 17, 2007. These applications are incorporated herein by reference in their entireties.

The present invention relates to a crystalline form and pharmaceutical compositions and uses of the crystalline form.

The mammalian enzyme PARP (a 113-kDa multidomain protein) has been implicated in the signalling of DNA damage through its ability to recognize and rapidly bind to DNA single or double strand breaks (D'Amours, et al., *Biochem. J.*, 342, 249-268 (1999)).

Several observations have led to the conclusion that PARP participates in a variety of DNA-related functions including gene amplification, cell division, differentiation, apoptosis, DNA base excision repair and also effects on telomere length and chromosome stability (d'Adda di Fagagna, et al., *Nature Gen.*, 23(1), 76-80 (1999)).

Studies on the mechanism by which PARP modulates DNA repair and other processes has identified its importance in the formation of poly (ADP-ribose) chains within the cellular nucleus (Althaus, F. R. and Richter, C., ADP-Ribosylation of Proteins: Enzymology and Biological Significance, Springer-Verlag, Berlin (1987)). The DNA-bound, activated PARP utilizes NAD to synthesize poly (ADP-ribose) on a variety of nuclear target proteins, including topoisomerase, histones and PARP itself (Rhun, et al., *Biochem. Biophys. Res. Commun.*, 245, 1-10 (1998))

Poly (ADP-ribosyl)ation has also been associated with malignant transformation. For example, PARP activity is higher in the isolated nuclei of SV40-transformed fibroblasts, while both leukemic cells and colon cancer cells show higher enzyme activity than the equivalent normal leukocytes and colon mucosa (Miwa, et al., *Arch. Biochem. Biophys.*, 181, 313-321 (1977); Burzio, et al., *Proc. Soc. Exp. Biol. Med.*, 149, 933-938 (1975); and Hirai, et al., *Cancer Res.*, 43, 3441-3446 (1983)).

A number of low-molecular-weight inhibitors of PARP have been used to elucidate the functional role of poly (ADP-ribosyl)ation in DNA repair. In cells treated with alkylating agents, the inhibition of PARP leads to a marked increase in DNA-strand breakage and cell killing (Durkacz, et al., *Nature*, 283, 593-596 (1980); Berger, N. A., *Radiation Research*, 101, 4-14 (1985)).

Subsequently, such inhibitors have been shown to enhance the effects of radiation response by suppressing the repair of potentially lethal damage (Ben-Hur, et al., *British Journal of Cancer*, 49 (Suppl. VI), 34-42 (1984); Schlicker, et al., *Int. J. Radiat. Bioi.*, 75, 91-100 (1999)). PARP inhibitors have been reported to be effective in radio sensitising hypoxic tumour cells (U.S. Pat. No. 5,032,617; U.S. Pat. No. 5,215,738 and U.S. Pat. No. 5,041,653).

Furthermore, PARP knockout (PARP −/−) animals exhibit genomic instability in response to alkylating agents and γ-irradiation (Wang, et al., *Genes Dev.*, 9, 509-520 (1995); Menissier de Murcia, et al., *Proc. Natl. Acad. Sci. USA*, 94, 7303-7307 (1997)).

A role for PARP has also been demonstrated in certain vascular diseases, septic shock, ischaemic injury and neurotoxicity (Cantoni, et al., *Biochim. Biophys. Acta*, 1014, 1-7 (1989); Szabo, et al., *J. Clin. Invest.*, 100, 723-735 (1997)). Oxygen radical DNA damage that leads to strand breaks in DNA, which are subsequently recognised by PARP, is a major contributing factor to such disease states as shown by PARP inhibitor studies (Cosi, et al., *J. Neurosci. Res.*, 39, 38-46 (1994); Said, et al., *Proc. Natl. Acad. Sci. U.S.A.*, 93, 4688-4692 (1996)). More recently, PARP has been demonstrated to play a role in the pathogenesis of haemorrhagic shock (Liaudet, et al., *Proc. Natl. Acad. Sci. U.S.A.*, 97(3), 10203-10208 (2000)).

It has also been demonstrated that efficient retroviral infection of mammalian cells is blocked by the inhibition of PARP activity. Such inhibition of recombinant retroviral vector infections was shown to occur in various different cell types (Gaken, et al., *J. Virology*, 70(6), 3992-4000 (1996)). Inhibitors of PARP have thus been developed for the use in antiviral therapies and in cancer treatment (WO 91/18591).

Moreover, PARP inhibition has been speculated to delay the onset of aging characteristics in human fibroblasts (Rattan and Clark, *Biochem. Biophys. Res. Comm.*, 201(2), 665-672 (1994)). This may be related to the role that PARP plays in controlling telomere function (d'Adda di Fagagna, et al., *Nature Gen.*, 23(1), 76-80 (1999)).

WO 2004/080976 discloses a number of phthalazinone derivatives, their activity in inhibiting PARP, and their consequential use in treating cancer, whether as an adjunct to radiotherapy or chemotherapy, or as a stand alone agent.

WO 2005/053662 describes the use of PARP inhibitors, in particular phthalazinone derivatives, as base excision repair (BER) inhibitors. The use of these inhibitors in the manufacture of medicaments for the treatment of cancers which are deficient in Homologous Recombination (HR) dependent DNA DSB repair activity, in particular for cancers which have a BRCA1 and/or a BRCA2 deficient phenotype, is described.

4-[3-(4-Cyclopropanecarbonyl-piperazine-1-carbonyl)-4-fluoro-benzyl]-2H-phthalazin-1-one (compound A) disclosed in WO 2004/080976:

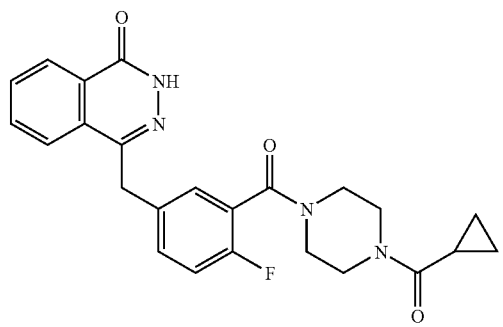

A is of particular interest.

A crystalline form of compound A (Form A) is disclosed in co-pending applications, which claim priority from U.S. 60/829,694, filed 17 Oct. 2006, entitled "Phthalazinone Derivative", including U.S. Ser. No. 11/873,671 and WO 2008/047082.

Particular forms of compound A may have advantageous properties, for example with regard to their solubility and/or their stability and/or their bioavailability and/or their impurity profile and/or their filtration characteristics and/or their drying characteristics and/or their lack of hygroscopicity, and/or they may be easier to handle and/or micronise and/or form into tablets.

Accordingly, a first aspect of the present invention provides 4-[3-(4-cyclopropanecarbonyl-piperazine-1-carbonyl)-4-fluoro-benzyl]-2H-phthalazin-1-one (compound A) substantially as crystalline Form L.

"Substantially as crystalline Form L" as used above, means that at least 50% by weight of compound A as Form L, preferably at least 70% by weight, 80% or 90% by weight. In some embodiments, at least 95% by weight, 99% by weight or even 99.5% or more by weight may be in crystalline form.

Compound A as crystalline Form L has an X-ray diffraction pattern ($\lambda$=1.5418 Å) containing specific peaks at:

| Peak | 2θ° (±0.1°) |
|------|-------------|
| 1 | 14.4 |
| 2 | 17.2 |
| 3 | 17.5 |
| 4 | 18.8 |
| 5 | 23.0 |

Compound A as crystalline Form L may also have the following additional peaks in an X-ray diffraction pattern ($\lambda$=1.5418 Å):

| Peak | 2θ° (±0.1°) |
|------|-------------|
| 6 | 10.4 |
| 7 | 13.6 |
| 8 | 25.1 |

Compound A as crystalline Form L may also be characterised by any combination of three or more peaks selected from the list of 8 peaks above.

A representative powder XRD pattern of compound A in Form L is shown in FIG. 1.

Form L of compound A is substantially free from solvent. The term "substantially free from solvent" as used herein refers to the form having only insignificant amounts of any solvent, e.g. a form with a total of 0.5% by weight or less of any solvent. The total amount of any solvent may be 0.25%, 0.1%, 0.05% or 0.025% by weight or less.

Form L of compound A may also be characterised using DSC. Form L of compound A when heated from 25° C. to 325° C. at 10° C. per minute will have an onset of melting at 198.5° C.±1° C. A representative DSC trace for compound A as Form L is shown in FIG. 2. The second endotherm corresponds to melting of Form A, to which the melted Form L transforms.

The second aspect of the present invention provides a method of obtaining 4-[3-(4-cyclopropanecarbonyl-piperazine-1-carbonyl)-4-fluoro-benzyl]-2H-phthalazin-1-one (compound A) as crystalline Form L from compound A as crystalline Form A.

This method involves slurrying compound A as either Form A or a mixture of Forms A and L in an organic solvent that may contain up to 30% water v/v. In some embodiments, the mixture may contain no Form L, or 99%, 90% or 80% as Form A. In other embodiments, the amount of Form L may be up to 50, 70 or even 80% of the mixture. In some embodiments, the organic solvent may contain no water. In other embodiments, the organic solvent may contain up to 25 or 20% water. The solvent may be selected from a solvent which gives sufficient solubility for a transformation to occur. In some embodiments, the solvent is selected from the group consisting of: methanol, ethanol, acetone, acetonitrile and nitromethane.

The slurrying may take place at a temperature up to the boiling point of the solvent, but may more usually be carried out at a temperature lower than that. In some embodiments, the slurrying takes place at between 20° C. and 50° C., or even 20° C. and 40° C., or 20° C. and 30° C. With lower temperatures, the slurrying time may be increased. Typically, the slurrying is carried out for at least 3 hours, at least 6 hours or even at least 24 hours. In some embodiments, the slurrying is carried out for at least 3 days, 4 days, a week or even 3 weeks.

A third aspect of the present invention provides a pharmaceutical composition comprising a compound of the first aspect and a pharmaceutically acceptable carrier or diluent.

An fourth aspect of the present invention provides a compound of the first aspect for use in a method of treatment of the human or animal body.

A fifth aspect of the present invention provides the use of a compound as defined in the first aspect of the invention in the preparation of a medicament for inhibiting the activity of PARP.

Further aspects of the invention provide the use of a compound as defined in the first aspect of the invention in the preparation of a medicament for the treatment of: vascular disease; septic shock; ischaemic injury; neurotoxicity; haemorraghic shock; viral infection; or diseases ameliorated by the inhibition of the activity of PARP.

Another further aspect of the invention provides for the use of a compound as defined in the first aspect of the invention in the preparation of a medicament for use as an adjunct in cancer therapy or for potentiating tumour cells for treatment with ionizing radiation or chemotherapeutic agents.

Other further aspects of the invention provide for the treatment of disease ameliorated by the inhibition of PARP, comprising administering to a subject in need of treatment a therapeutically-effective amount of a compound as defined in the first aspect, preferably in the form of a pharmaceutical composition and the treatment of cancer, comprising administering to a subject in need of treatment a therapeutically-effective amount of a compound as defined in the first aspect in combination, preferably in the form of a pharmaceutical composition, simultaneously or sequentially with ionizing radiation or chemotherapeutic agents.

In further aspects of the present invention, the compounds may be used in the preparation of a medicament for the treatment of cancer which is deficient in Homologous Recombination (HR) dependent DNA DSB repair activity, or in the treatment of a patient of a cancer which is deficient in HR dependent DNA DSB repair activity, comprising administering to said patient a therapeutically-effective amount of the compound.

The HR dependent DNA DSB repair pathway repairs double-strand breaks (DSBs) in DNA via homologous mechanisms to reform a continuous DNA helix (K. K. Khanna and S. P. Jackson, Nat. Genet. 27(3): 247-254 (2001)). The components of the HR dependent DNA DSB repair pathway include, but are not limited to, ATM (NM_000051), RAD51 (NM_002875), RAD51L1 (NM_002877), RAD51C(NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY (Hughes-Davies, et al., *Cell,* 115, pp 523-535). HR components are also described in Wood, et al., *Science,* 291, 1284-1289 (2001).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterised in the art (see for example, Wood, et al., *Science,* 291, 1284-1289 (2001)) and include the components listed above.

In some preferred embodiments, the cancer cells may have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (Hughes-Davies, et al., *Cell,* 115, 523-535).

BRCA1 and BRCA2 are known tumour suppressors whose wild-type alleles are frequently lost in tumours of heterozygous carriers (Jasin M., *Oncogene,* 21(58), 8981-93 (2002); Tuft, et al., *Trends Mol. Med.,* 8(12), 571-6, (2002)). The association of BRCA1 and/or BRCA2 mutations with breast cancer is well-characterised in the art (Radice, P. J., *Exp Clin Cancer Res.,* 21(3 Suppl), 9-12 (2002)). Amplification of the EMSY gene, which encodes a BRCA2 binding factor, is also known to be associated with breast and ovarian cancer.

Carriers of mutations in BRCA1 and/or BRCA2 are also at elevated risk of cancer of the ovary, prostate and pancreas.

In some preferred embodiments, the individual is heterozygous for one or more variations, such as mutations and polymorphisms, in BRCA1 and/or BRCA2 or a regulator thereof. The detection of variation in BRCA1 and BRCA2 is well-known in the art and is described, for example in EP 699 754, EP 705 903, Neuhausen, S. L. and Ostrander, E. A., *Genet. Test,* 1, 75-83 (1992); Chappnis, P. O. and Foulkes, W. D., *Cancer Treat Res,* 107, 29-59 (2002); Janatova M., et al., *Neoplasma,* 50(4), 246-50 (2003); Jancarkova, N., *Ceska Gynekol.,* 68(1), 11-6 (2003)). Determination of amplification of the BRCA2 binding factor EMSY is described in Hughes-Davies, et al., *Cell,* 115, 523-535).

Mutations and polymorphisms associated with cancer may be detected at the nucleic acid level by detecting the presence of a variant nucleic acid sequenc or at the protein level by detecting the presence of a variant (i.e. a mutant or allelic variant) polypeptide.

Use

Figure 1:
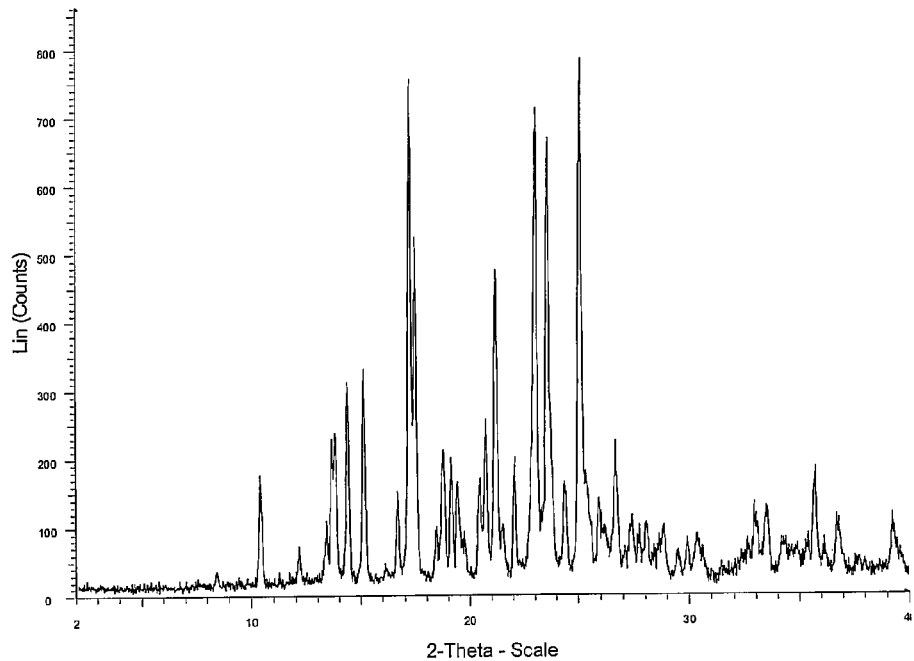
FIG. 1 shows a representative powder XRD pattern of compound A as Form L.
Figure 2:
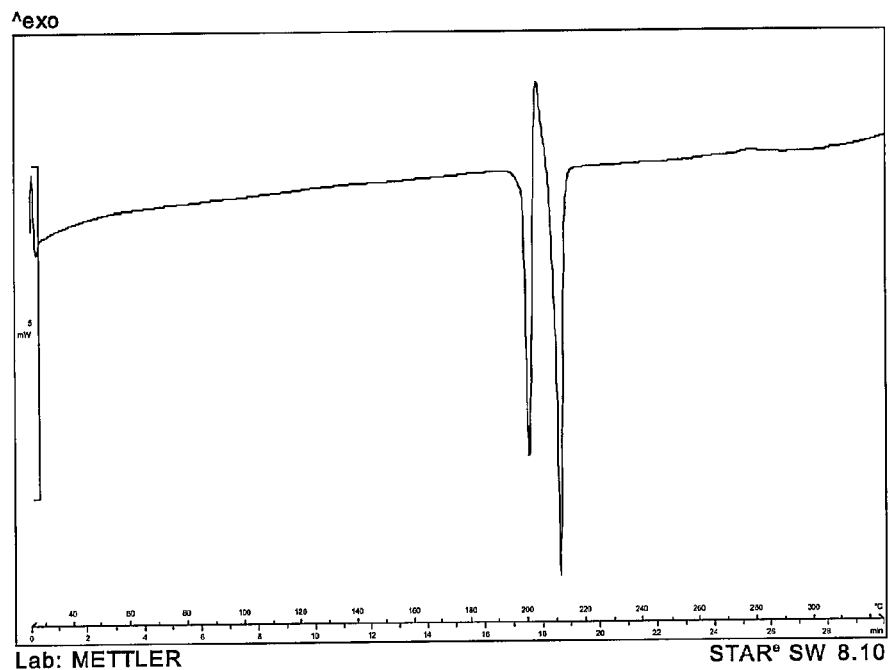
FIG. 2 shows a representative DSC trace of compound A as Form L obtained by heating from 25° C. to 325° C. at 10° C. per minute.

The present invention provides compound A as Form L as an active compound, specifically, active in inhibiting the activity of PARP.

The term "active" as used herein, pertains to the compound which is capable of inhibiting PARP activity. One assay which may conveniently be used in order to assess the PARP inhibition offered by the compound is described in the examples below.

The present invention further provides a method of inhibiting the activity of PARP in a cell, comprising contacting said cell with an effective amount of the active compound, preferably in the form of a pharmaceutically acceptable composition. Such a method may be practised in vitro or in vivo.

For example, a sample of cells may be grown in vitro and the active compound brought into contact with said cells, and the effect of the compound on those cells observed. As examples of "effect", the amount of DNA repair effected in a certain time may be determined. Where the active compound is found to exert an influence on the cells, this may be used as a prognostic or diagnostic marker of the efficacy of the compound in methods of treating a patient carrying cells of the same cellular type.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "adjunct" as used herein relates to the use of the active compound in conjunction with known therapeutic means. Such means include cytotoxic regimes of drugs and/or ionising radiation as used in the treatment of different cancer types. In particular, the active compounds are known to potentiate the actions of a number of cancer chemotherapy treatments, which include the topoisomerase class of poisons (e.g. topotecan, irinotecan, rubitecan), most of the known alkylating agents (e.g. DTIC, temozolamide) and platinum based drugs (e.g. carboplatin, cisplatin) used in treating cancer.

The active compound may also be used as cell culture additives to inhibit PARP, for example, in order to sensitize cells to known chemotherapeutic agents or ionising radiation treatments in vitro.

The active compound may also be used as part of an in vitro assay, for example, in order to determine whether a candidate host is likely to benefit from treatment with the compound in question.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

Formulations

While it is possible for the active compound to be administered alone, it is preferable to present it as a pharmaceutical composition (e.g., formulation) comprising the active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing the active compound, as defined above, together with one or more pharmaceutically acceptable carriers, excipients, buffers, adjuvants, stabilisers, or other materials, as described herein, such that active compound remains as crystalline Form L.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, "Handbook of Pharmaceutical Additives", 2nd Edition (eds. M. Ash and I. Ash), 2001 (Synapse Information Resources, Inc., Endicott, N.Y., USA), "Remington's Pharmaceutical Sciences", 20th edition, pub. Lippincott, Williams & Wilkins, 2000; and "Handbook of Pharmaceutical Excipients", 2nd edition, 1994.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of suspensions, tablets, granules, powders, capsules, cachets, pills or pastes.

Formulations suitable for oral administration (e.g., by ingestion) may be presented as discrete units such as capsules, cachets or tablets, each containing a predetermined amount of the active compound; as a powder or granules; as a suspension in an aqueous or non-aqueous liquid; or as a paste.

A tablet may be made by conventional means, e.g. compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

A capsule may include the active compound in suspension.

Formulations suitable for topical administration (e.g. transdermal, intranasal, ocular, buccal, and sublingual) may be formulated as a paste.

Formulations suitable for topical administration to the eye also include eye drops wherein the active compound is suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Dosage

It will be appreciated that appropriate dosages of the active compound, and compositions comprising the active compound, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 10 mg to about 600 mg per $m^2$ body area weight of the subject per day.

EXAMPLES

General Methods

Powder XRD

Powder X-ray diffraction was recorded with a Bruker D5000 diffractometer (wavelength of X-rays 1.5418 Å Cu source, Voltage 40 kV, filament emission 40 mA). Samples were scanned from 2-40° 2θ using a 0.02° step width and a 1 second time count.

Differential Scanning Calorimetry (DSC)

DSC was recorded using a Mettler DSC820E with TS0801RO robotic system. Typically less than 5 mg of material, contained in a 40 μl aluminium pan fitted with a pierced lid, was heated over the temperature range 25° C. to 325° C. at a constant heating rate of 10° C. per minute. A nitrogen purge gas was used with flow rate 100 ml per minute.

Obtaining Compound A as Form A

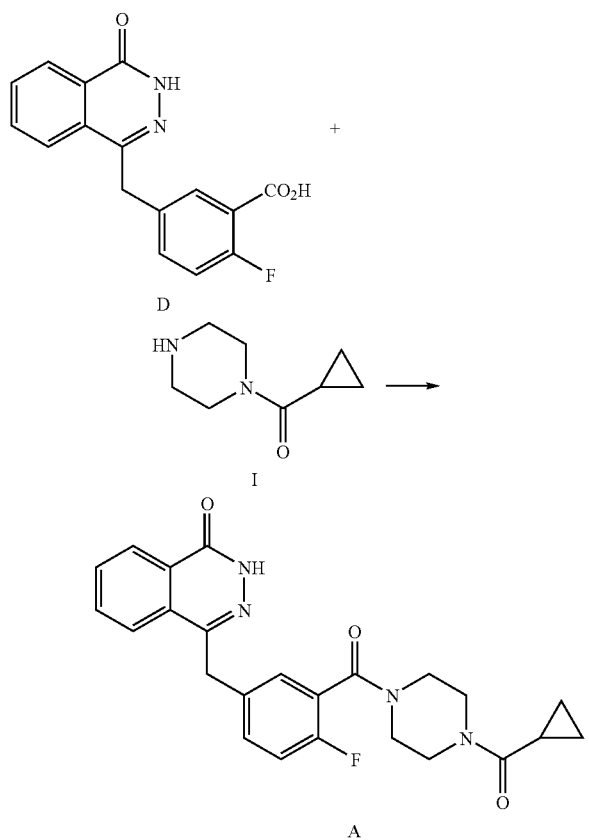

NMR $^1$H NMR spectra were recorded using Bruker DPX 400 spectrometer at 400 MHz. Chemical shifts were reported in parts per million (ppm) on the δ scale relative to tetramethylsilane internal standard. Unless stated otherwise all samples were dissolved in DMSO-$d_6$.

Mass Spectra

Mass spectra were recorded on an Agilent XCT ion trap mass spectrometer using tandem mass spectrometry (MS/MS) for structural confirmation. The instrument was operated in a positive ion electrospray mode.

(a) 4-[3-(4-Cyclopropanecarbonyl-piperazine-1-carbonyl)-4-fluoro-benzyl]-2H-phthalazin-1-one (Compound A)

2-Fluoro-5-[(4-oxo-3,4-dihydrophthalazin-1-yl)methyl] benzoic acid (D)(15.23 g, 51.07 mmol) was suspended with stirring under nitrogen in acetonitrile (96 ml). Diisopropylethylamine (19.6 ml, 112.3 mmol) was added followed by 1-cyclopropylcarbonylpiperazine (I)(9.45 g, 61.28 mmol) and acetonitrile (1 ml). The reaction mixture was cooled to 18° C. 0-Benzotriazol-1-yl-tetramethyluronium hexafluorophosphate (25.18 g, 66.39 mmol) was added over 30 minutes and the reaction mixture was stirred for 2 hours at room temperature. The reaction mixture was cooled to 3° C. and maintained at this temperature for 1 hour, before being filtered. The filter cake was washed with cold (3° C.) acetonitrile (20 ml) before being dried in vacuo at up to 40° C. to give the title compound as a pale yellow solid (20.21 g).

Mass Spectrum: MH+ 435

1H NMR (400 MHz, DMSO-d6) δ: 0.70 (m, 4H), 1.88 (br s, 1H), 3.20 (br s, 2H), 3.56 (m, 6H), 4.31 (s, 2H), 7.17 (t, 1H), 7.34 (dd, 1H), 7.41 (m, 1H), 7.77 (dt, 1H), 7.83 (dt, 1H), 7.92 (d, 1H), 8.25 (dd, 1H), 12.53 (s, 1H).

(b) Recrystallisation of Compound a from Ethanol 4-(3-{[4-(cyclopropylcarbonyl)piperazin-1-yl]carbonyl}-4-fluorobenzyl)phthalazin-1(2H)-one (compound A) (20.00 g, 44.66 mmol) was suspended in a mixture of water (50 ml) and ethanol (150 ml). The suspension was heated to reflux with stirring. The solution produced was then cooled to 70° C. and filtered. The filter pad was washed with a mixture of water (8 ml) and ethanol (22 ml).

The filtrate was cooled to 45° C. with stirring. 4-(3-{[4-(cyclopropylcarbonyl)piperazin-1-yl]carbonyl}-4-fluorobenzyl)phthalazin-1(2H)-one (Compound A) in Form A (0.08 g) was added in order to seed the mixture. The resulting suspension was cooled to 20° C. over 2.5 hours and was stirred at this temperature for a further 16 hours in order to establish crystallisation. Water (200 ml) was added over 5 hours maintaining the temperature at 20° C. At the end of the addition the suspension was held at 20° C. for 2 hours.

The suspension was filtered and the filter cake washed with a mixture of ethanol (24 ml) and water (56 ml). The isolated solid was discharged and dried under vacuum at 40-60° C., to give the compound A as Form A as an off white solid (18A g).

Figure 3:
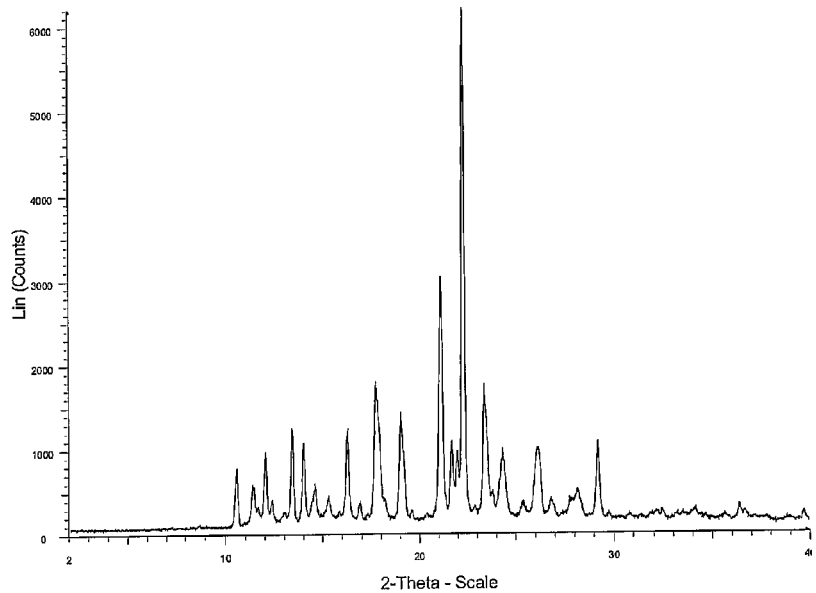
FIG. 3 shows a representative powder XRD pattern of compound A as Form A.
Figure 4:
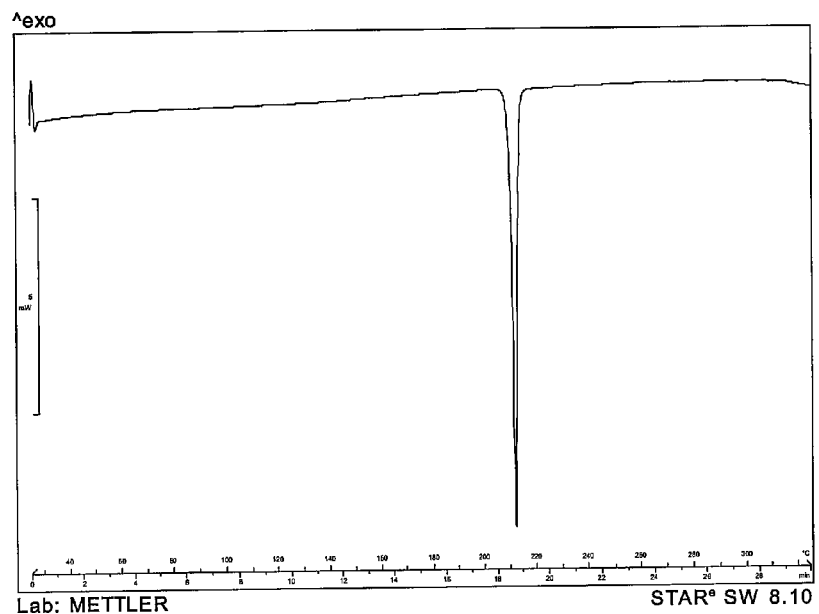
FIG. 4 shows a representative DSC trace of compound A as Form A obtained by heating from 25° C. to 325° C. at 10° C. per minute.

FIG. 3 shows a representative powder XRD pattern of compound A as Form A and FIG. 4 shows a representative DSC trace of compound A as Form A obtained by heating from 25° C. to 325° C. at 10° C. per minute. The XRD pattern was obtained as set out above, but with a 4 second time count.

Compound A as crystalline Form A has an X-ray diffraction pattern (λ=1.5418 Å) containing specific peaks at:

| Peak | 2θ° (±0.1°) |
| --- | --- |
| 1 | 12.0 |
| 2 | 17.8 |
| 3 | 21.1 |
| 4 | 22.3 |
| 5 | 29.2 |

Compound A as crystalline Form A may also have the following additional peaks an X-ray diffraction pattern (λ=1.5418 Å):

| Peak | 2θ° (±0.1°) |
|---|---|
| 6 | 10.5 |
| 7 | 14.0 |
| 8 | 21.7 |
| 9 | 24.3 |
| 10 | 26.1 |

Compound A as crystalline Form A may also be characterised by any combination of three or more peaks selected from the list of 10 peaks above.

Form A of compound A when heated from 25° C. to 325° C. at 10° C. per minute by DSC will have an onset of melting at 210.1° C.±1° C.

Example 1

23 mg of compound A as Form A was weighed into a vial. To this solid was added 0.25 mL of a solution made from 8.5 mL methanol and 1.5 mL water (i.e. 15% water v/v). The resulting slurry was heated to 70° C., filtered and allowed to cool slowly to ambient temperature in a capped vial. The resulting crystallisation yielded a solid which was dried by a vacuum oven. The product is compound A as Form L.

Example 2

Approximately 50 mg of compound A as Form A was added to a reaction tube and approximately 1 ml of ethanol/water (80:20 v/v) added. The mixture was slurried at 40° C. for 3 weeks. The sample was filtered and dried on the filter for 10 minutes before allowing to dry on the bench overnight. The product is compound A as Form L.

Example 3

In a similar manner to Example 2, compound A as Form A was slurried in an ethanol/water (80:20 v/v) mixture for 3 weeks at 60° C. to yield compound A as Form L.

Example 4

Approximately 30 mg of compound A as Form A was added to a reaction tube and about 1 ml of ethanol/water (80:20 v/v) added to form a saturated suspension of Form A. To this saturated suspension, 30 mg of compound A as Form L was added. The mixture was slurried at 25° C. for 3 days. The sample was filtered and dried on the filter for 10 minutes before allowing to dry on the bench overnight. The product is compound A as Form L, with no Form A.

Example 5

Example 4 was repeated but using the following solvents to slurry the mixture of Form A and Form L—for these experiments samples were slurried for 4 days.

| Mixture | Solvent(s) |
|---|---|
| a | Acetone |
| b | Acetonitrile |
| c | Ethanol |
| d | Methanol |
| e | Nitromethane |

In each case, the product is compound A as crystalline Form L, with no Form A.

Example 6

Inhibitory Action

In order to assess the inhibitory action of the active compound, the following assay was used to determine an $IC_{50}$ value.

Mammalian PARP, isolated from Hela cell nuclear extract, was incubated with Z-buffer (25 mM Hepes (Sigma); 12.5 mM $MgCl_2$ (Sigma); 50 mM KCl (Sigma); 1 mM DTT (Sigma); 10% Glycerol (Sigma) 0.001% NP-40 (Sigma); pH 7.4) in 96 well FlashPlates (TRADE MARK) (NEN, UK) and varying concentrations of said inhibitors added. All compounds were diluted in DMSO and gave final assay concentrations of between 10 and 0.01 µM, with the DMSO being at a final concentration of 1% per well. The total assay volume per well was 40 µl.

After 10 minutes incubation at 30° C. the reactions were initiated by the addition of a 10 µl reaction mixture, containing NAD (5 µM), $^3$H-NAD and 30mer double stranded DNA-oligos. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 µl 30% acetic acid to each well. The plates were then shaken for 1 hour at room temperature.

The plates were transferred to a TopCount NXT (TRADE MARK) (Packard, UK) for scintillation counting. Values recorded are counts per minute (cpm) following a 30 second counting of each well.

The % enzyme activity for the compound is then calculated using the following equation:

$$\% \text{ Inhibition} = 100 - \left(100 \times \frac{(cpm \text{ of unknowns} - \text{mean negative } cpm)}{(\text{mean positive } cpm - \text{mean neagative } cpm)}\right)$$

$IC_{50}$ values (the concentration at which 50% of the enzyme activity is inhibited) were calculated, which are determined over a range of different concentrations, normally from 10 µM down to 0.001 µM. Such $IC_{50}$ values are used as comparative values to identify increased compound potencies.

Compound A has an $IC_{50}$ of about 5 nM.

Potentiation Factor

The Potentiation Factor ($PF_{50}$) for the active compound is calculated as a ratio of the $IC_{50}$ of control cell growth divided by the $IC_{50}$ of cell growth+PARP inhibitor. Growth inhibition curves for both control and compound treated cells are in the presence of the alkylating agent methyl methanesulfonate (MMS). The test compound was used at a fixed concentration of 0.2 micromolar. The concentrations of MMS were over a range from 0 to 10 µg/ml.

Cell growth was assessed using the sulforhodamine B (SRB) assay (Skehan, P., et al., (1990) New colorimetric cytotoxicity assay for anticancer-drug screening. J. Natl. Cancer Inst. 82, 1107-1112.). 2,000 HeLa cells were seeded into each well of a flat-bottomed 96-well microtiter plate in a volume of 100 µl and incubated for 6 hours at 37° C. Cells were either replaced with media alone or with media containing PARP inhibitor at a final concentration of 0.5, 1 or 5 µM. Cells were allowed to grow for a further 1 hour before the addition of MMS at a range of concentrations (typically 0, 1, 2, 3, 5, 7 and 10 μg/ml) to either untreated cells or PARP inhibitor treated cells. Cells treated with PARP inhibitor alone were used to assess the growth inhibition by the PARP inhibitor.

Cells were left for a further 16 hours before replacing the media and allowing the cells to grow for a further 72 hours at 37° C. The media was then removed and the cells fixed with 100 μl of ice cold 10% (w/v) trichloroacetic acid. The plates were incubated at 4° C. for 20 minutes and then washed four times with water. Each well of cells was then stained with 100 μl of 0.4% (w/v) SRB in 1% acetic acid for 20 minutes before washing four times with 1% acetic acid. Plates were then dried for 2 hours at room temperature. The dye from the stained cells was solubilized by the addition of 100 μl of 10 mM Tris Base into each well. Plates were gently shaken and left at room temperature for 30 minutes before measuring the optical density at 564 nM on a Microquant microtiter plate reader.

Compound A has a $PF_{50}$ at 200 nM of at least 20.

The invention claimed is:

1. 4-[3-(4-cyclopropanecarbonyl-piperazine-1-carbonyl)-4-fluoro-benzyl]-2H-phthalazin-1-one as crystalline Form L.

2. The compound of claim 1 having the following characteristic peaks in a powder XRD:

| Peak | 2θ° (±0.1°)<br>(λ = 1.5418 Å) |
|------|-------------------------------|
| 1 | 14.4 |
| 2 | 17.2 |
| 3 | 17.5 |
| 4 | 18.8 |
| 5 | 23.0 |

3. The compound of claim 1 having the following characteristic peaks in a powder XRD:

| Peak | 2θ° (±0.1°)<br>(λ = 1.5418 Å) |
|------|-------------------------------|
| 1 | 14.4 |
| 2 | 17.2 |
| 3 | 17.5 |
| 4 | 18.8 |
| 5 | 23.0 |
| 6 | 10.4 |
| 7 | 13.6 |
| 8 | 25.1. |

4. The compound of claim 1, which has an onset of melting at 198.5° C.±1° C. when heated from 25° C. to 325° C. at 10° C. per minute in DSC.

5. A method of obtaining 4-[3-(4-cyclopropanecarbonyl-piperazine-1-carbonyl)-4-fluoro-benzyl]-2H-phthalazin-1-one as crystalline Form L from 4-[3-(4-cyclopropanecarbonyl-piperazine-1-carbonyl)-4-fluoro-benzyl]-2H-phthalazin-1-one as crystalline Form A, comprising slurrying 4-[3-(4-cyclopropanecarbonyl-piperazine-1-carbonyl)-4-fluoro-benzyl]-2H-phthalazin-1-one as either Form A or a mixture of Forms A and L in an organic solvent selected from the group consisting of methanol, ethanol, acetone, acetonitrile and nitromethane; that optionally contains up to 30% water v/v.

6. A pharmaceutical composition comprising a compound having crystalline Form L according to claim 1 and a pharmaceutically acceptable carrier or diluent.

7. A compound having crystalline Form L according to claim 1 for use in a method of treatment of the human or animal body.

8. A compound having crystalline Form L according to claim 1 for the use in a method of inhibiting PARP in the treatment of the human or animal body.

* * * * *